United States Patent [19]
Saito et al.

[11] Patent Number: 5,179,084
[45] Date of Patent: Jan. 12, 1993

[54] ANTIVIRAL PHOSPHORIC ACID ESTERS OF OXETANOCINS

[75] Inventors: Seiichi Saito, Kashiwa; Shigeru Hasegawa; Masayuki Kitagawa, both of Urawa; Nobuyoshi Shimada; Katsutoshi Takahashi, both of Tokyo; Jun-ichi Seki, Takasaki; Hiroo Hoshino, Maebashi; Yukihiro Nishiyama, Aichi; Kenichi Matsubara, Suita; Takemitsu Nagahata, Toyonaka, all of Japan

[73] Assignee: Nippon Kayaku Kabushiki Kaisha, Tokyo, Japan

[21] Appl. No.: 504,393

[22] Filed: Apr. 4, 1990

[30] Foreign Application Priority Data

Apr. 10, 1989 [JP] Japan .................. 1-087961
Nov. 16, 1989 [JP] Japan .................. 1-296232
Nov. 17, 1989 [JP] Japan .................. 1-297443

[51] Int. Cl.$^5$ ............... A61K 31/675; C07F 9/6512
[52] U.S. Cl. ............................ 514/81; 514/87; 544/243; 544/244
[58] Field of Search ............ 544/243, 244; 514/81, 514/86

[56] References Cited

U.S. PATENT DOCUMENTS

| | | | |
|---|---|---|---|
| 4,594,321 | 6/1986 | Fujishima et al. | 544/244 X |
| 4,743,689 | 5/1988 | Shimada et al. | 544/277 |
| 4,845,215 | 7/1989 | Shimada et al. | 544/265 |
| 4,855,466 | 8/1989 | Zahler et al. | 549/546 |
| 4,857,075 | 4/1990 | Borthwick et al. | 514/262 |
| 4,918,075 | 4/1990 | Zahler | 514/262 |
| 4,950,758 | 8/1990 | Vince et al. | 544/276 |

FOREIGN PATENT DOCUMENTS 0284405  9/1988  European Pat. Off. ............ 544/243

OTHER PUBLICATIONS

Gemershausen, et al. Chemical Abstracts, vol. 100:17143e (1984).
Niitsuma, et al., Tetrahedron Letters, vol. 28(34), pp. 3967-3970 (1987).

Primary Examiner—Diana G. Rivers
Attorney, Agent, or Firm—Nields & Lemack

[57] ABSTRACT

The present invention relates to phosphoric acid esters of oxetanocins having an antiviral activity which are represented by general formula (I):

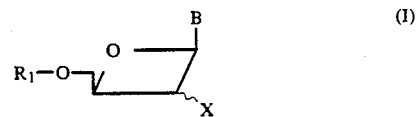

wherein $R_1$ represents a phosphoric acid ester residue, X represents hydrogen, hydroxy or hydroxymethyl group, and B represents a purine base residue, and pharmacologically acceptable salts thereof.

4 Claims, No Drawings

ANTIVIRAL PHOSPHORIC ACID ESTERS OF OXETANOCINS

BACKGROUND OF THE INVENTION

1. Field Of The Invention

The present invention relates to phosphoric acid esters of oxetanocins having an antiviral activity which are represented by general formula (I):

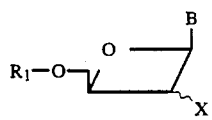

wherein $R_1$ represents a phosphoric acid ester residue, X represents hydrogen, hydroxy or hydroxymethyl group, and B represents a purine base residue, and pharmacologically acceptable salts thereof.

2. Description Of The Prior Art

Oxetanocin itself is disclosed in Journal of Antibiotics, Vol. 39, No. 11, Pages 1623-25 (1986), EP-A$_2$-0 182 312, etc.

The derivatives thereof are described in Journal of Antibiotics, Vol. 40, No. 12, page 1788-90 (1987); EP-A-0 291 917 and EP-A-0 334 250.

It is also known in view of the publications described above that these compounds exhibit an antiviral activity.

At the present time, however, no satisfactory therapeutic drug is available for viral diseases. It is thus desired to develop a novel antiviral agent.

SUMMARY OF THE INVENTION

Accordingly, an object of the present invention is to provide phosphoric acid esters of oxetanocins useful as new antiviral agents.

The phosphoric acid esters of oxetanocins in accordance with the present invention exhibit an antiviral action including an activity for inhibiting reverse transcriptase (RTase) of RNA virus (e.g., human immunodeficiency virus simply referred to as HIV), an anti-RNA viral activity, for example, anti-HIV activity anti-heptatitis non A non B viral activity, an anti-DNA viral activity, for example, anti-hepatitis B viral activity, an anti-cytomegalovirus activity, an anti-helpes simplex I or II viral activity, an anti-varicella-zoster viral activity and the like, and are expectedly useful as drugs for treating HIV, or as antiviral agents such as hepatitis B antiviral agents, anti-cytomegaloviral agents, anti-varicella-zoster viral agents and the like.

DETAILED DESCRIPTION OF THE INVENTION

As a result of various investigations, the present inventors have found that phosphoric acid esters of oxetanocins which are represented by general formula (I):

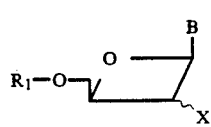

(wherein $R_1$ represents a phosphoric acid ester residue, B represents a purine base residue, and X represents H, OH or CH$_2$OH) exhibit an activity of inhibiting reverse transcriptase of HIV, an anti-HIV activity, an activity of inhibiting DNA polymerase of DNA virus and an anti-DNA viral activity. The present invention has thus been accomplished.

As the phosphoric acid ester residue in the present invention, there are illustratively shown:

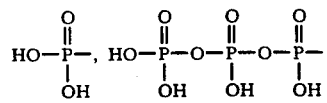

The purine base residue means residues of purine derivatives linked to an oxetane ring at the 9-position of purine skeleton represented by the following formula:

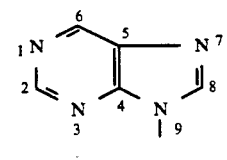

Examples of the purine base residue include adenine residue, guanine residue, hypoxanthine residue, 2-aminoadenine residue, and the like.

Concrete examples of the compound of general formula (I) are listed in Table 1.

In Table 1 in the formulas, the meanings of the abbreviations are as follows:

A: adenine residue

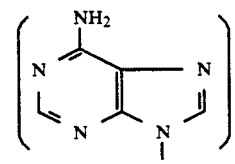

G: guanine residue

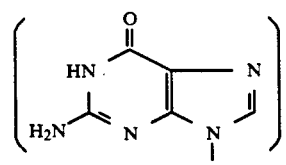

H: hypoxanthine residue

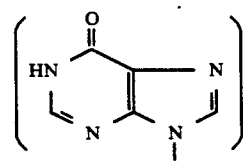

D: 2-aminoadenine residue

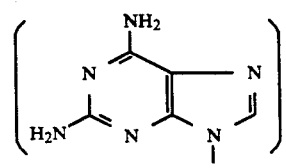

TABLE 1

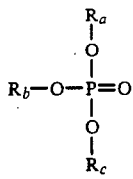

| Compound No. | B | R₁ | X |
|---|---|---|---|
| 1 | A | $HO-\underset{OH}{\underset{|}{\overset{O}{\overset{\|}{P}}}}-$ | $CH_2OH$ |
| 2 | A | $HO-\underset{OH}{\underset{|}{\overset{O}{\overset{\|}{P}}}}-O-\underset{OH}{\underset{|}{\overset{O}{\overset{\|}{P}}}}-O-\underset{OH}{\underset{|}{\overset{O}{\overset{\|}{P}}}}-$ | $CH_2OH$ |
| 3 | G | $HO-\underset{OH}{\underset{|}{\overset{O}{\overset{\|}{P}}}}-O-\underset{OH}{\underset{|}{\overset{O}{\overset{\|}{P}}}}-O-\underset{OH}{\underset{|}{\overset{O}{\overset{\|}{P}}}}-$ | $CH_2OH$ |
| 4 | D | $HO-\underset{OH}{\underset{|}{\overset{O}{\overset{\|}{P}}}}-O-\underset{OH}{\underset{|}{\overset{O}{\overset{\|}{P}}}}-O-\underset{OH}{\underset{|}{\overset{O}{\overset{\|}{P}}}}-$ | $CH_2OH$ |
| 5 | G | $HO-\underset{OH}{\underset{|}{\overset{O}{\overset{\|}{P}}}}-$ | $CH_2OH$ |
| 6 | A | $HO-\underset{OH}{\underset{|}{\overset{O}{\overset{\|}{P}}}}-$ | H |
| 7 | A | $HO-\underset{OH}{\underset{|}{\overset{O}{\overset{\|}{P}}}}-$ | OH |
| 8 | A | $HO-\underset{OH}{\underset{|}{\overset{O}{\overset{\|}{P}}}}-$ | OH |

The compounds of general formula (I) in accordance with the present invention can be obtained as follows.

Monophosphoric acid esters of oxetanocins represented by general formula (Ia):

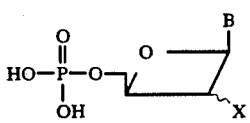

(Ia)

wherein X represents H, OH or CH₂OH and B represents a purine base residue, can be obtained by reacting oxetanocins represented by general formula (II):

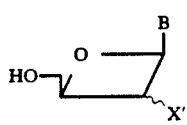

(II)

wherein X' represents H, OH, —O—P₃ or —CH₂—O—P₃ (wherein P₃ is a protecting group) and B represents a purine base residue with phosphorus oxyhalogenide such as phosphorus oxychloride in the presence of lower alkyl phosphates represented by the general formula below:

$$R_b-O-\underset{\underset{R_c}{\overset{|}{O}}}{\overset{\overset{R_a}{\overset{|}{O}}}{\overset{|}{P}}}=O$$

(wherein $R_a$, $R_b$ and $R_c$ each independently represents hydrogen or a lower alkyl group) and, when X' is —OP₃ or —CH₂—O—P₃, then eliminating the protecting group from the protected compounds.

The reaction may generally be carried out at a temperature of from about −20° C. to about −50° C., preferably from about −10° C. to about 20° C. using the trilower alkyl phosphate as a solvent, although the reaction may also be carried out in an organic solvent inert to the reaction.

The removal of the protecting group P₃ can be effected in a conventional manner. As P₃, protecting groups which are removable by catalytic reduction are generally used and hence, the protecting groups are removed by catalytic reduction using a noble metal catalyst. As such, a catalyst used for the catalytic reduction, platinum, Pd, Pd-C, etc. can be used. It is preferred that catalytic reduction be conducted generally in a solvent. Polar solvents such as water, lower alcohols, lower alkyl ketones, lower fatty acids, etc. can be used.

The reaction may be carried out at a temperature of from about 0° C. to the boiling point of a solvent (e.g., about 150° C.).

As the protecting groups which are removable by the catalytic reduction, there are used benzyl groups (which may be unsubstituted or substituted with a lower alkyl, a lower alkoxy, a halogen, etc.).

Alternatively, the protecting group of P₃ may be lower alkyl carbonyl, lower alkyl silyl, or the like. In the case of these protecting groups, the groups may be eliminated in a conventional manner, for example, by hydrolysis, etc.

Next, triphosphoric acid esters of oxetanocin-related compounds are described below.

The triphosphoric acid esters of oxetanocin-related compounds represented by general formula (Ib):

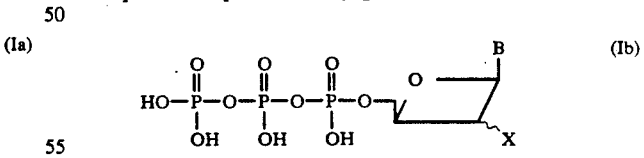

(Ib)

(wherein X and B have the same significances as described above), can be obtained by reacting the monophosphoric acid esters of oxetanocins represented by general formula (Ia) with carbonyldiimidazole and trialkylammonium pyrophosphates in the presence of trialkylamines.

The reaction is performed generally in a polar solvent such as a lower alcohol, a lower alkyl ketone, a cyclic ketone, a lower fatty acid, etc.

The reaction may be carried out at temperature of about 0° C. to the boiling point of a solvent (e.g., about 150° C.).

Based on 1 mole of the compound represented by general formula (Ia), approximately 1 to 10 mols of trilower alkyl ($C_1$–$C_5$) amines and approximately 2 to 10 mols of carbonyldiimidazole such as dicyclohexylcarbodiimido are used.

The desired compound can be separated by conventional chromatography or the like.

In the present invention, the alkyl group in the lower alkyl, lower alcohol, etc. has generally 1 to 5 carbon atoms. Examples of the alkyl group include methyl, ethyl, propyl, butyl, pentyl, etc. The alkyl group may also be branched.

The compound of the present invention forms salts with alkalis. As the alkalis for forming the salts, there are shown alkali hydroxides and the like. For forming the salts, alkalis may be reacted with the compound of general formula (I) generally in a solvent, in a conventional manner.

Next, production process of a typical compound of general formula (I) wherein B is adenine residue (A) will be briefly described below, including production process of the compound of general formula (II). In the formulas below, A-$P_2$ represents a group shown by:

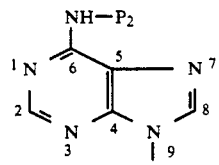

wherein $P_2$ represents a protecting group.

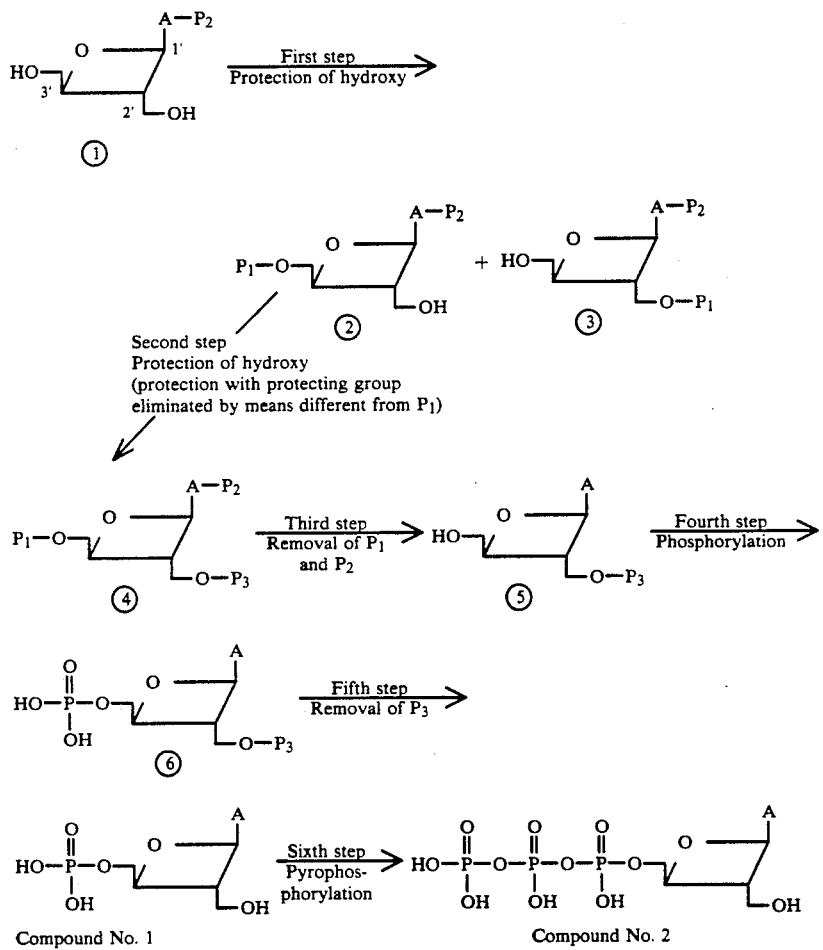

Each of the steps mentioned above will be explained below.

Step 1: The hydroxy group in 2'—$CH_2OH$ of N(6)-protected oxetanocin ① is selectively protected with some protecting group.

As the protecting group ($P_1$ or $P_2$ in the formulas) of compounds ② and ③, formyl group or a lower alkyl carbonyl group which may optionally be substituted (with a substituent such as halogen atom, lower alkoxy, benzoyl, etc.); an acyl group such as acetyl, chloroacetyl, trichloroacetyl, methoxyacetyl, pivaloyl, phenoxyacetyl, trityloxyacetyl, benzoyl, etc.; and optionally substituted lower alkyl groups including unsubstituted lower alkyl groups such as t-butyl and the like, and substituted lower alkyl groups such as unsubstituted trityl and substituted trityls such as lower alkoxy-trityls, e.g., monomethoxytrityl, dimethoxytrityl, trimethoxytrityl, and the like can be referred to. Further, silyl type protecting groups, i.e., silyl groups having various substituents, e.g., trimethylsilyl, t-butyldimethylsilyl, t-butyldiphenylsilyl and the like can also be mentioned.

The above-described protecting group can be introduced according to hitherto known methods. Preferably, a protecting group which can be eliminated effectively at a later step is chosen. Compound ② and compound ③ can be separated from each other by column chromatography.

Step 2: This is a step for protecting the hydroxy group in 3'—CH₂OH. When P₁ is acyl group or silyl group, it is preferred to use as the protecting group a benzyl group, an allyl group, etc. which is removable by reduction, etc.

Step 3: This is a step for eliminating the protecting groups P₁ and P₂. In the case that P₁ is a silyl group having various substituents thereon, n-tetrabutylammonium fluoride in tetrahydrofuran can be used. In the case that P₂ is an acyl group, sodium methoxide or ammonia water, etc. can be used.

Step 4: This is a step for phosphorylation. As phosphoric acids used for the phosphorylation, phosphorus oxychloride can be used. The phosphorylation is generally carried out in the presence of tri-lower alkyl phosphates.

Step 5: This is a step for eliminating the protecting group of the hydroxyl group in 2'—CH₂OH. In the case that the protecting group for P₃ is such a group like benzyl group as being removable through reduction, catalytic reduction using palladium-carbon, etc. is generally used. By this step, Compound No. 1 (monophosphoric acid ester) can be obtained.

Step 6: This is a step for pyrophosphorylation. The triphosphate can be obtained by reacting with carbonyldiimidazole in the presence of tributylamine, and then reacting with tri-lower alkyl ammonium pyrophosphate such as tributylammonium pyrophosphate, etc.

Next, the compound of this invention is explained with the biological activity below.

The compound of the present invention exhibits an excellent antiviral activity and can be used as antiviral agents.

As viruses against which the antiviral activity is expectedly effective, there are the following: DNA virus:
pox virus, herpes virus, adenovirus, papovavirus, hepanavirus, parvovirus RNA virus:
rahbdovirus, firovirus, paramyxovirus, orthomyxovirus, arenavirus, retrovirus, coronavirus, bunyavirus, togavirus, flavivirus, calicivirus, picornavirus, reovirus The compounds of general formula (I) are expectedly useful as agents for treating various viral diseases, for example, herpes, hepatitis B, infectious diseases caused by cytomegalovirus, varicella-zoster virus, AIDS, etc.

The compounds of general formula (I) wherein B is an adenine residue or a hypoxanthine residue are excellent especially in an inhibiting action against RNA virus such as HIV, etc. or DNA virus such as cytomegalo virus, varicella-zoster virus, etc.

Furthermore, the compounds of general formula (I) wherein B is a guanine residue or a 2-aminoadenine residue are excellent especially in an inhibiting action against growth of DNA virus such as hepatitis B virus, cytomegalovirus, etc.

Monophosphates of oxetanocins represented by general formula (Ia):

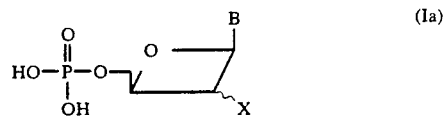

(wherein X is H, OH or —CH₂OH and B is a purine base residue), which are compounds of general formula (I) wherein R₁ is a monophosphoric acid ester, can prevent growth of the virus by administering an effective dose of the compounds (Ia) to virus-infected warm-blooded animal (including human).

Next, test examples and examples of the present invention will be illustrated below.

TEST EXAMPLE 1

Measurement of Activity of Reverse Transcriptase (RTase) of HIV

1. Standard enzyme

MOLT-4/HTLV-IIIB cells which were persistently infected with HIV were destroyed with Triton X-100 or the like to prepare crude enzyme (RTase).

Using poly(dT) and oligo(dA) as template primers, the following reaction solution was used.

2. Composition of reaction solution

| | |
|---|---|
| 5 mg/ml Bovine serum albumin | 2.5 μl |
| 1M Tris-HCl buffer (pH 7.8) | 2.0 |
| 100 mM Dithiothreitol | 2.0 |
| 1M KCl | 2.25 |
| 10 mM Poly(dT) | 1.0 |
| 150 μM dATP | 4.5 |
| 5 units/ml Oligo(dA) | 4.0 |
| 1.25 mM MnCl₂ | 2.5 |
| 1 mCi/ml ³H-dATP | 2.25 |
| RTase | 10.0 |
| Distilled water | 27.0 |
| Total | 60.0 |

3. Reaction conditions

37° C., 1 hour

Uptake of ³H-AMP in the acid-insoluble fraction in the reaction solution under the above conditions was determined by a liquid scintillation counter.

The RTas inhibitory activity of the present compound is shown in Table 2.

TABLE 2

| Inhibition of HIV RTase by This Compound | |
|---|---|
| Compound No. 2 (μM) | RTase Inhibition (%) |
| 417 | 98.8 |
| 125 | 93.0 |
| 42.7 | 69.4 |
| 12.5 | 33.9 |
| 4.17 | 1.0 |
| 0 | 0 |

EXAMPLE 1

(Synthesis of Compound Nos. 1 and 2)

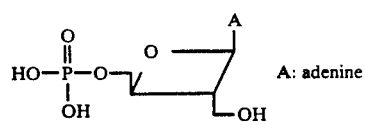

A: adenine

Synthesis of Compounds (2) and (3)

To a solution of 123 mg of N(6)-benzoyl-9-(2-deoxy-2-hydroxymethyl-β-D-erythroxetanosyl)adenine [Compound (1)] ($P_2 = COC_6H_5$) in 1 ml of anhydrous dimethylformamide were added 70 mg of imidazole and a solution of 60 mg of tert-butyldimethylsilyl chloride in 2 ml of anhydrous dimethylformamide. The mixture was stirred at room temperature for 2 hours. The solvent was distilled off under reduced pressure and 20 ml of water was added to the residue. The mixture was extracted with chloroform. After washing the chloroform extract with saturated sodium chloride aqueous solution, the extract was dried over anhydrous sodium sulfate. Sodium sulfate was filtered off and the solvent was distilled off under reduced pressure to give light yellow syrup. The syrup was subjected to column chromatography using 20 g of silica and eluted with chloroform-methanol (20:1). The fractions having Rf value of about 0.46 in silica gel TLC [developing solvent: chloroform-methanol (10 1)] were collected. The solvent was distilled off under reduced pressure to give 49.6 mg (30.6%) of Compound (2) ($P_2 = -COC_6H_5$, $P_1 =$

Furthermore, the fractions having Rf value of about 0.60 were collected and the solvent was distilled off under reduced pressure to give 25.3 mg (16.0%) of Compound (3) ($P_2 = -COC_6H_5$, $P_1 =$

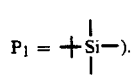

Compound (2): MS m/z: 470 (M+H)+; NMR (400MHz, CDCl$_3$, TMS) ppm: 9.23 (1H, s, NH), 8.78 (1H, s, 8—H), 8.68 (1H, s, 2-H), 8.03 (2H, d, J=7.5Hz, Ph), 8.50-8.63 (3H, m, Ph), 6.60 (1H, d, J=5.6Hz, 1'-H), 4.73 (1 H, m, 3'-H), 3.93—

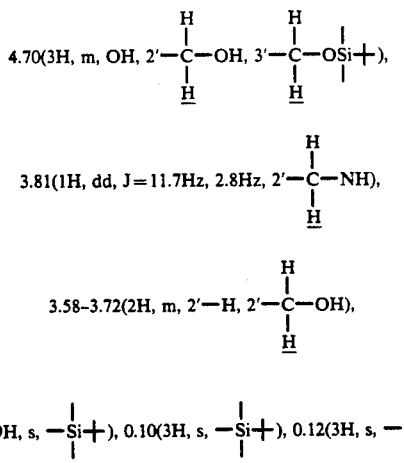

Compound (3): MS m/z: 470 (M+H)+; NMR (400MHz, CDCl$_3$, TMS) ppm: 9.34 (1H, s, NH), 8.79 (1H, s, 8-H), 8.34 (1H, s, 2—H), 8.35 (2H, d, J=7.5Hz, Ph), 7.48-7.63 (3H, m, Ph), 6.50 (1H, d, J=5.7Hz, 1'—H), 5.50 (1H, broad s, —OH), 4.04 (2H, m, 3'—CH$_2$OH), 3.67-3.87 (3H, m, 2'-H, 2'—CH$_2$OH), 0.91 (9H, s,

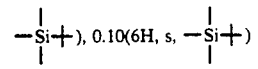

Synthesis of Compound (4)

Under ice cooling, 25 mg of sodium hydride was suspended in 3 ml of anhydrous tetrahydrofuran under a stream of nitrogen and a solution of 100 mg of Compound (2) in 3 ml of anhydrous tetrahydrofuran was added to the suspension. After stirring for 30 minutes, 26 μl of benzyl bromide was added to the mixture followed by stirring at room temperature for 2 hours. To the reaction solution was added 3 ml of saturated ammonium chloride aqueous solution. After stirring at room temperature for 20 minutes, the solvent was distilled off under reduced pressure. After 5 ml of water was added to the residue, the mixture was extracted 3 times with 10 ml of chloroform. After washing with saturated sodium chloride aqueous solution, the organic phase was dried over anhydrous sodium sulfate. Sodium sulfate was filtered off and the solvent was distilled off under reduced pressure to give syrup. The syrup was separated by means of silica gel column chromatography [20 ml, chloroform-methanol (50:1)] to give 96.4 mg (yield, 85.6%) of Compound (4) ($P_2 = -COC_6H_5$,

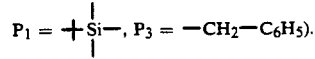

Compound (4): NMR (60MHz, CDCl$_3$, TMS) ppm: 9.29 (1H, br s, NH), 8.73 (1H, s, 8-H), 8.62 (1H, s, 2-H), 7.70-8.10 (2H, m), 7.17-7.60 (8H, m), 6.60 (1H, d, J=6.2Hz, 1'-H), 4.40-4.87 (3H, m), 3.50-4.10 (5H, m), 1.98 (9H, s,), 1.20 (6H, s)

Synthesis of Compound (5)

To a solution of 96.4 mg of Compound (4) in 2 ml of tetrahydrofuran was added 0.3 ml of 1.05M tetrahydrofuran solution of tetrabutylammonium fluoride. The mixture was stirred at room temperature for an hour. The solvent was removed from the reaction solution by distillation under reduced pressure to give the residue. To the residue were added 1.5 ml of methanol and 1.5 ml of conc. ammonia water. The resulting mixture was stirred at 60° C. for 2 hours. The reaction solution was concentrated to dryness under reduced pressure. The residue was dissolved in 3 ml of methanol and 800 mg of silica gel was added to the solution. The solvent was distilled off under reduced pressure. The residue was laminated onto 50 ml of silica gel column equilibrated with chloroform-methanol (20:1) and eluted with chloroform-methanol (20:1, 10:1) to give 43 mg (yield, 72.6%) of Compound (5) ($P_3 = -CH_2-C_6H_5$).

Compound (5): NMR (60MHz, CD$_3$OD, TMS) ppm: 8.65 (1H, s, 8—H), 8.23 (1H, s, 2—H), 7.32 (5H, s, ⌀CH$_2$—O—), 6.33 (1H, d, 6.0Hz, 1'—H), 4.60 (2H, s, ⌀—CH$_2$—), 3.66-4.18 (5H, m)

Synthesis of Compound ⑥

Under cooling at −20° C., 0.3 ml of phosphorus oxychloride was added to a suspension of 322 mg of Compound ⑤ in 6 ml of triethyl phosphate under a stream of nitrogen. The mixture was then stirred at 0° C. for 18 hours. After adding to 10 ml of saturated sodium bicarbonate aqueous solution, the reaction solution was extracted 3 times with 15 ml of chloroform. After 100 ml of water was added to the aqueous phase, the mixture was passed through a column packed with 60 ml of DEAE-Sephadex A-25 (carbonate type) followed by washing with 200 ml of water. Then, the aqueous phase was eluted with 300 ml of 0.1M triethylamine-carbonate buffer (pH 7.48) and then with 500 ml of 0.3M triethylaminecarbonate buffer (pH 7.38). The fractions having Rf value of about 0.37 were collected by silica gel TLC [butanol:acetic acid:water (12:3:5)] to give crude Compound ⑥ ($P_3 = -CH_2-C_6H_5$).

Compound ⑥: NMR (60MHz, $CD_3OD$): 8.66 (1H, s, 8—H), 8.20 (1H, s, 2—H), 7.30 (5H, s, Ph), 6.60 (1H, d, J=6.2Hz, 1'—H), 4.60 (2H, s), 4.10–4.34 (2H, m), 3.66–4.03 (3H, m)

Synthesis of Compound No. 1

In a mixture of 20 ml of ethanol, 7 ml of water and 3 ml of acetic acid, was dissolved 416 mg of crude Compound ⑥ and, 40 mg of 10% palladium-carbon was added to the solution. While heating to reflux, catalytic reduction was carried out for 3 hours. The reaction solution was filtered and the catalyst was removed. The filtrate was then concentrated under reduced pressure to give colorless residue. The residue was dissolved in 50% hydrated methanol and separation was effeced by means of column chromatography using Sephadex LH-20 ® (400 ml) equilibrated with the same solvent. The fractions having Rf value of about 0.13 were collected by silica gel TLC [butanol-acetic acid:water (12:3:5)] and the solvent was distilled off under reduced pressure. The residue was dissolved in 5 ml of water and pH was adjusted to 1.8 with 0.1N hydrochloric acid. The thus pH-adjusted solution was passed through a column of MCl ® GEL CHP 20P (120 ml). After washing with water, the solution was eluted with 80% hydrated methanol. The solvent was distilled off under reduced pressure to give 138 mg of Compound No. 1 as colorless powders.

Compound No. 1: FD-MS (m/z): 332 $(M+H)^+$; NMR (200MHz, $D_2O$) ppm: 8.73 (1H, s, 8—H), 8.12 (1H, s, 2—H), 6.45 (1H, d, J=5.7Hz, 1'—H), 4.84 (1H, m), 4.09 (2H, m), 3.74–3.93 (3H, m)

Synthesis of Compound No. 2

To a solution of 111 mg of Compound No. 1 in 3.5 ml of anhydrous dimethylformamide were added 160 μl of tributylamine and 271.6 mg of carbonyl diimidazole. After stirring at room temperature for 5 hours, 107 μl of methanol was added to the mixture followed by stirring for 30 minutes. A solution of 603 mg of tributylammonium pyrophosphate in 8 ml of dimethylformamide was then added to the mixture followed by stirring at room temperature for 18 hours. The formed precipitates were filtered and washed with dimethylformamide. The filtrate and washing liquid were collected. After an equal volume of methanol was added thereto, the mixture was concentrated to dryness under reduced pressure. The residue was dissolved in water and the solution was passed through a column packed with 50 ml of DEAE-Sephadex A-25 (carbonate type). After eluting with 370 ml each of linear gradient (0.05→0.4 M) of triethylamine-carbonate buffer (pH 7.5), elution was conducted with 0.4M of the same buffer. The main product-eluted fraction was collected and concentrated to dryness under reduced pressure. Methanol was added to the concentrate and azeotropically distilled to effect desalting. The residue was dissolved in 10 ml of water and under iced cooling, pH was adjusted to 2.0 with 0.1N hydrochloric acid and then adjusted to 7.0 with 1N sodium hydroxide. The thus pH-adjusted solution was passed through a column packed with 6 ml of activated characoal powders. After washing with 2% sodium chloride aqueous solution and then with water, the solution was eluted with ethanol-1.5% ammonia water (1:1). The fractions having Rf value of about 0.02 were collected and concentrated to dryness under reduced pressure to give 70 mg of Compound No. 2 as the sodium salt.

Compound No. 2: FAB-MS (m/z): 492 $(M+H)^+$, 514 $(M+Na)^+$, 536 $(M+2Na-H)^+$, 558 $(M+3Na-2H)^+$; NMR (200MHz, $D_2O$) ppm: 8.78 (1H, s, 8H), 8.08 (1H, s, 2—H), 6.44 (1H, d, J=5.5Hz, 1'—H), 4.83 (1H, m), 4.25 (2H, m), 3.80–4.00 (3H, m)

EXAMPLE 2

(Synthesis of Compound Nos. 3 and 5)

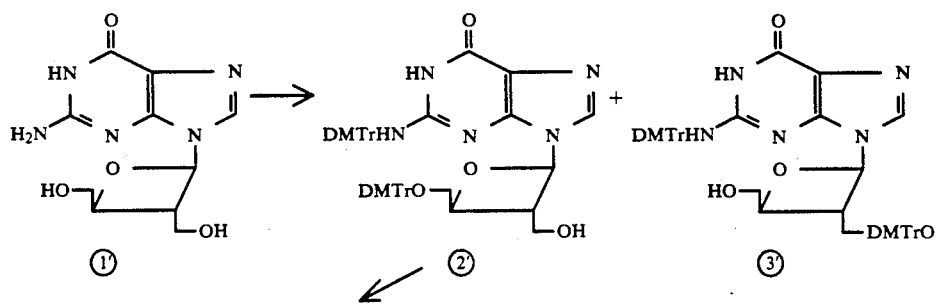

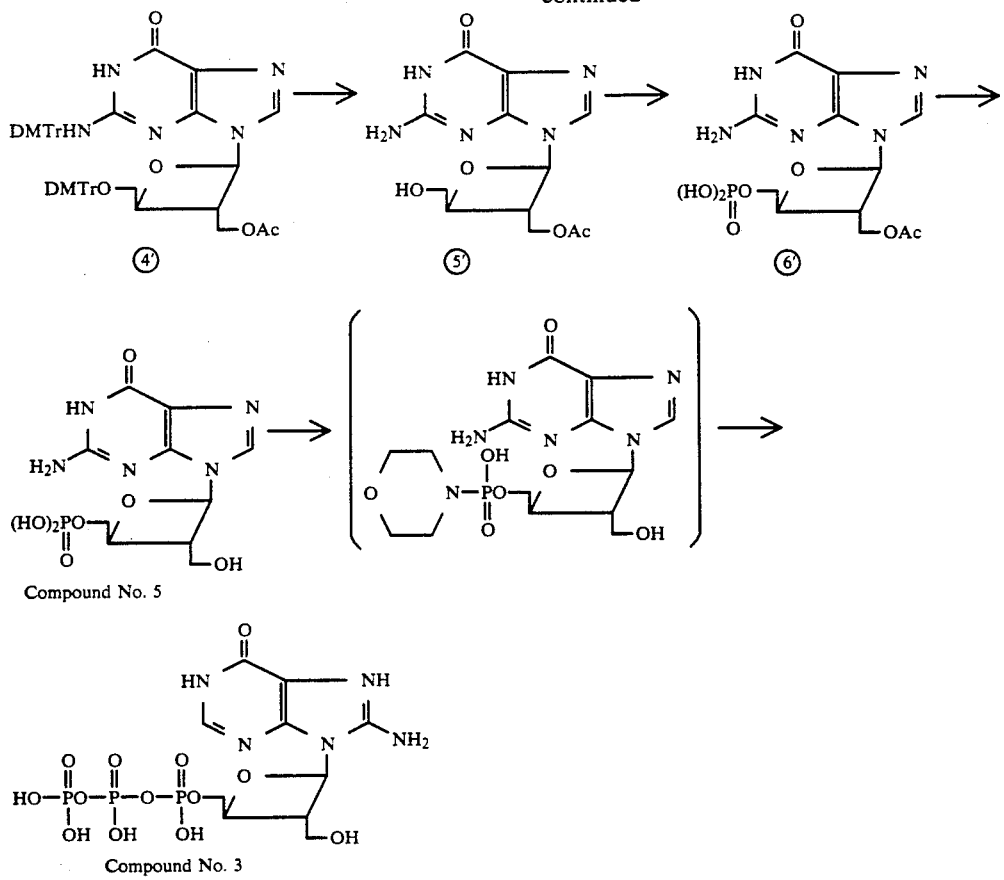

Compound No. 5

Compound No. 3

(1) Synthesis of Compounds ② and ③'

Under a stream of nitrogen, 86.7 μl of triethylamine and 139.3 mg of 4,4'-dimethoxytrityl chloride were added to a solution of 50 mg of Compound ① [oxetanocin-G (OXT-G)] in 1.6 ml of anhydrous dimethylformamide. The mixture was stirred at room temperature for 24 hours under light shielding. The solvent was distilled off under reduced pressure and the resulting syrup was separated by silica gel column chromatography (20 ml, chloroform-methanol=50:1). The fractions having Rf value of about 0.51 were collected by silica gel TLC [developing solvent: chloroform-methanol 10:1)]. The solvent was distilled off under reduced pressure to give 27.1 mg (16.6%) of Compound ③ as colorless powders. Furthermore the fractions having Rf value of about 0.64 were collected and the solvent was distilled off under reduced pressure to give 42.0 mg (25.8%) of Compound ②.

Compounds ②: MS (FAB) 873 (M+H)+ NMR (CDCl$_3$, ppm): 7.65 (s, 1H), 7.5–6.6 (m, 27H), 5.32 (d, 1H), 4.60 (m, 1H), 3.70–3.62 (4s, 12H), 3.74–3.2 (m, 4H), 3.01 (m, 1H)

Compounds ③: MS (FAB) 873 (M+H)+ NMR (CD$_3$OD, ppm): 8.21 (s, 1H), 7.4–6.6 (m, 26H), 5.49 (d, 1H), 4.29 (m, 1H), 3.76 (2s, 6H), 3.60 (2s, 6H), 3.7–3.0 (m, 5H)

(2) Synthesis of Compound ④

Compound ② (1.73 g), a catalytic amount of N,N-dimethylaminopyridine, 331 μl of triethylamine and 196 μl of acetic anhydride were added to 30 ml of anhydrous . and the mixture was stirred at room temperature for 40 minutes. After completion of the reaction, the solvent was distilled off and 50 ml of water was added to the residue. The mixture was extracted twice with chloroform (50 ml). After chloroform was distilled off, the resulting syrup was isolated and purified by column chromatography (300 ml, chlorform-methanol =40:1) to give 1.51 g of Compound ④

TLC (silica gel): Rf=0.55 (chloroform-methanol =10:1)

NMR (CDCl$_3$, ppm): 7.67 (s, 1H), 7.5–6.6 (m, 27H), 5.83 (d, 1H), 4.53 (m, 1H), 3.92 (m, 2H), 3.77–3.70 (4s, 12H), 3.35 (m, 2H), 3.23 (m, 1H), 2.06 (s, 3H)

(3) Synthesis of Compound ⑤'

In 50 ml of 80% acetic acid was dissolved 1.51 g of Compound ④ and the solution was stirred at room temperature for 5 hours. After completion of the reaction, the reaction solution was concentrated to dryness. The residue was crystallized from methanol to give 0.5 g of Compound ⑤.

TLC (silica gel): Rf=0.38 (n-butanol:acetic acid :water=4:1:2)

MS (FAB): 310 (M+H)+

NMR (DMSO-d$_6$, ppm): 8.25 (s, 1H), 6.55 (bs, 1H), 6.15 (d, 1H), 5.28 (m, 1H), 4.48 (m, 1H), 4.30 (m, 2H), 3.9–3.1 (m, 3H), 2.03 (s, 3H)

(4) Synthesis of Compound ⑥'

Under cooling at −20° C., 76.8 μl of phosphorus oxychloride was added to a suspension of 55 mg of Compound ⑤ in 1.53 ml of triethyl phosphate under a stream of nitrogen. The mixture was then stirred at 0° C. overnight. After adding to 5 ml of saturated sodium hydrogencarbonate aqueous solution, the reaction solution was extracted twice with 5 ml of chloroform. After 150 ml of water was added to the aqueous phase, the mixture was passed through a column packed with 50 ml of DEAE-Sephadex ® A-25 (carbonate type) followed by washing with 50 ml of water and then, eluted with 170 ml of 0.1M triethylamine-carbonate buffer (pH 7.48) and then with 170 ml of 0.4M triethylamine-carbonate buffer (pH 7.38). The main product-eluted fraction was concentrated to dryness under reduced pressure to give 71.5 mg of crude Compound ⑥.

TLC (silica gel): Rf=0.16 (2-propanol:conc. ammonia water:water=7:1:2) MS (FAB): 390 (M+H)+, 412 (M+Na)+ NMR (D₂O, ppm): 8.29 (s, 1H), 6.30 (d, 1H), 4.82 (m, 1H), 4.34 (m, 2H), 4.09 (m, 2H), 3.94 (m, 1H), 2.04 (s, 3H)

(5) Synthesis of Compound No. 5

After 71 mg of crude Compound ⑥ was dissolved in 5 ml of water, 4.67 ml of 0.1N sodium hydroxide was added to the solution. The mixture was stirred at room temperature for 53 hours. After completion of the reaction, the reaction mixture was adjusted to pH of 1.5 with 0.1N hydrochloric acid. After 50 ml of water was further added thereto, the thus pH-adjusted solution was passed through a column packed with MCI ® GEL CHP 20P (80 ml). The main product was eluted with water and concentrated to dryness under reduced pressure to give 44.3 mg of Compound No. 5.

TLC (silica gel): Rf=0.13 (2-propanol:conc. ammonia water:water=7:1:2)
MS (FAB): 348 (M+H)+
NMR (D₂O, ppm): 8.89 (s, 1H), 6.41 (d, 1H), 4.84 (m, 1H), 4.10 (m, 2H), 3.87 (m, 2H), 3.70 (m, 1H)

(6) Synthesis of Compound No. 3

After 50 mg of Compound No. 5, 1.4 ml of t-butanol and 48.9 μl of 4-morpholine were dissolved in 1.4 ml of water, a solution of 118.4 mg of dicyclohexylcarbodiimide in 2 ml of t-butanol was dropwise added to the solution over 30 minutes. After completion of the reaction, t-butanol was distilled off and 5 ml of ether was then added for extraction. After the aqueous phase was concentrated to dryness under reduced pressure, a solution of 186.6 mg of tributylammonium pyrophosphate in 3 ml of dimethylsulfoxide was added to the resulting residue. The mixture was stirred at 37° C. for 2 days. After completion of the reaction, 200 ml of water was added and the mixture was passed through a column packed with 10 ml of activated charcoal powders. After washing with 2% sodium chloride aqueous solution and then with water, elution was performed with 70% aqueous methanol. After the eluate was evaporated to dryness under reduced pressure, the residue was dissolved in 200 ml of water and the solution was passed through a column packed with 50 ml of DEAE-Sephadex A-25 (carbonate type). After eluting with 500 ml each of linear gradient (0.1M→0.4M) of triethylaminelinear carbonate buffer (pH 7.3), elution was further conducted with 0.4M triethylamine carbonate buffer containing 0.5 M sodium salt. After the main product-eluted fraction was adjusted to pH of 2.2 with 1N hydrochloric acid and then adjusted to pH of 7.0 with 1N sodium hydroxide. The thus pH-adjusted solution was passed through a column packed with 3 ml of activated charcoal. After washing with 2% sodium chloride aqueous solution and then with water, the solution was eluted with 70% aqueous methanol-1.5% ammonia water. The eluate was concentrated to dryness under reduced pressure to give mg of Compound No. 3 as the sodium salt.

MS (FD): 508 (M+H)+, 576 (M+3Na)+
³¹P-NMR (D₂O, ppm): −3.28 (d, 1P), −7.49 (d, 1 P), −18.50 (t, 1 P)
¹H-NMR (D₂O, ppm): 8.33 (s, 1H), 6.29 (d, 1H), 4.82 (m, 1H), 4.27 (m, 2H), 3.87 (m, 3H)

Example 3

(Synthesis of Compound No. 6)

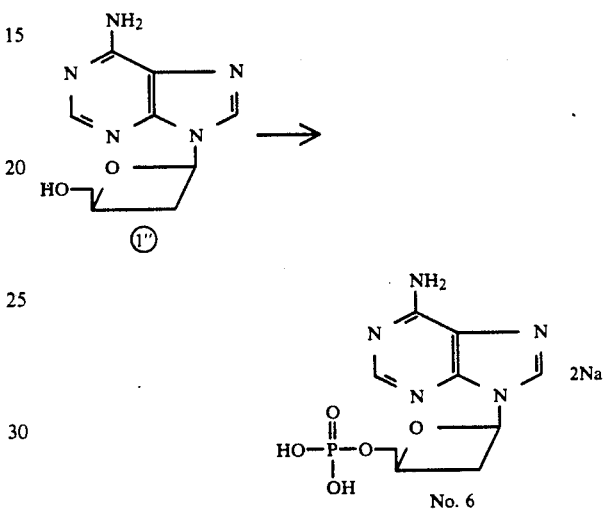

Under cooling at −20° C., 15.1 μl of phosphorus oxychloride was added to a suspension of 7.7 mg of Compound ①″ in 300 l of triethyl phosphate under a stream of nitrogen. The mixture was then stirred at 0° C. overnight. After neutralizing with 3 ml of saturated sodium hydrogencarbonate aqueous solution, the reaction solution was extracted twice with 5 ml of chloroform. After 60 ml of water was added to the aqueous phase, the mixture was passed through a column packed with 12 ml of DEAE-Sephadex ® A-25 (carbonate type) followed by washing with water and then, the aqueous phase was eluted with 75 ml of 0.1M triethylamine-carbonate buffer (pH 7.0) and then with 75 ml of 0.4M triethylamine-carbonate buffer (pH 7.3). The main product-eluted fraction was collected and adjusted to pH of 2.0 with 1N hydrochloric acid, and then to pH of 7.0 with 1N sodium hydroxide. The pH-adjusted solution was passed through a column packed with 2 ml of activated charcoal. After washing with 2% sodium chloride aqueous solution and then with water, the solution was eluted with 80% aqueous methanol. The eluate was concentrated to dryness to give 3.0 m of Compound No. 6 as the sodium salt.

UVmax (nm) 257 (0.01N HCl)
MS (FAB) 302 (M+H)+, 324 (M+Na)+
NMR (D₂O, ppm) 8.92 (s, 1H), 8.18 (s, 1H), 6.67 (t, 1H), 5.02 (m, 1H) 3.94 (m, 2H), 3.4–3.1 (m, 2H)

In the case that the compounds of the present invention are used as antiviral agents, they are administered singly or as admixtures with excipients or carriers in the form of an injection, an oral agent, suppository, or the like. As the excipients or carriers, pharmaceutically acceptable ones are chosen and kind and composition are determined by route of administration or method of administration. As a liquid carrier, there are used, for example, water, alcohol or animal or vegetable oils such as soybean oil, peanut oil, sesami oil, mineral oil, etc. or synthetic oils. As a solid carrier, there are used, for example, sugars such as maltose, sucrose, etc.; amino acids; cellulose derivatives such as hydroxypropyl cellulose, etc.; organic acid salts such as magnesium stearate, etc. In the case of an injection, it is generally preferred to use physiological saline, various buffer solutions, solutions of sugars such as glucose, inositol, mannitol, etc.; glycols such as ethylene glycol, polyethylene glycol, etc. Alternatively, the compounds of the present invention may also be freeze dried together with excipients such as sugars, e.g., inositol, mannitol, glucose, mannose, maltose, sucrose, etc., amino acids such as phenylalanine, etc. and upon administration, the freeze dried preparations are dissolved in a suitable solvent for injection, for example, sterile water, physiological saline, glucose solution, electrolyte solution, liquid for intravenous administration such as amino acids, etc. and the resulting solutions are administered.

A quantity of the compound of the present invention contained in the preparation may vary depending upon the form of preparation but is generally in the range of from 0.1 to 100 wt %, preferably 1 to 90 wt %. For example, in the case of injection, it is sufficient that the compound of the present invention be contained generally in 0.1 to 5 wt %. In the case of oral administration, the compound of the present invention is used in the form of tablets, capsules, powders, granules, liquid, dry syrup, etc., together with the aforesaid solid carriers or liquid carriers. In the case of capsules, tablets, granules and powders, the content of the compound of the present invention is generally approximately 3 to 100 wt %, preferably 5 to 90 wt %. The balance is carriers.

A dose is determined depending upon age, body weight or condition of patients, purpose of treatment, etc. but a therapeutic dose is generally in a range of 1 to 300 mg/kg/day for parenteral administration and for oral administration, in a range of 5 to 500 mg/kg/day.

The compounds of the present invention are characterized in that they have low toxicity and any of the compounds has a small accumulation in toxicity even after continuous administration. Even though the compound of the present invention is administered in a single dose of 800 mg/kg, any toxic sign was not noted.

Next, examples of preparations are given below.

Preparation Example 1

(Freeze dried injection)

Purified water is added to 30 parts by weight (hereafter the same, unless otherwise indicated) of Compound No. 1 to make the whole weight 200 parts. After the compound is dissolved, the solution is sterilized and filtered through a millipore filter GS type. Two grams of this filtrate are taken in a vial bottle of 10 ml and freeze dried to give a freeze dried injection containing 30 mg of Compound No. 1.

PREPARATION EXAMPLE 2

(Granules)

Fifty parts of Compound No. 5,600 parts of lactose, 330 parts of crystalline cellulose and 20 parts of hydroxypropyl cellulose are thoroughly kneaded and the mixture is compressed using a roll type compressor (Roller Compacter ®). After grinding into powders, sieving is performed so as to distribute between 16 mesh and 60 mesh to prepare granules.

PREPARATION EXAMPLE 3

(Tablets)

Thirty parts of Compound No. 5,120 parts of crystalline lactose, 147 parts of crystalline cellulose and 3 parts of magnesium stearate are tabletted using a V-shaped kneader to give tablets, one tablet weighing 300 mg.

Next, the anti-cytomegalovirus activity and anti-HIV activity of the compounds of the present invention and the inhibitory action on DNA polymerase of hepatitis B virus (HBV) are described below by referring to specific examples.

TEST EXAMPLE 2

Anti-cytomegalovirus activity was determined by the following manner. A 35 mmΦ dish containing a single layer of human fetal fibroblasts was infected with 100 PFU (plaque forming units) of cytomegalovirus (A0169 strain). After adsorption for one hour, a medium (0.5% agarose, 2% fetal calf serum) containing a varied concentration of the compound of the present invention was superposed thereon, and the whole was cultured at 37° C. for 10 days in 5% (v/v) carbon dioxide incubator, after which the formation of plaque was measured. The results are shown in Table 3 in terms of 50% inhibitory value ($ED_{50}$).

TABLE 3

| Compound No. | Anti-cytomegalovirus Activity $ED_{50}$ (μg/ml) |
|---|---|
| 1 | 1.85 |
| 5 | 0.4 |

TEST EXAMPLE 3

Anti-HIV (Human Immunodeficiency Virus) Activity

MT-4 cell (about 10,000 cells/ml) was added to a 24 well tray, and then 100 μl of a solution containing a predetermined quantity of Compound No. 1 of the present invention was added. After culturing at 37° C. for 5 hours in 5% (v/v) carbon dioxide incubator, $10^3$ to $10^4$ infection units of HIV was added and cultured for 4 days. Then, a part of the cultured fluid was coated onto a slide glass and immobilized with acetone, after which development of virus antigen was observed by indirect fluorescent antibody method.

As the primary antibody of the fluorescent antibody method, a serum of AIDS patient was used. As its secondary antibody, FITC-labelled human IgG was used.

TABLE 4

| Anti-HIV Activity of the Compound Nos. 1 and 6 of This Invention | |
|---|---|
| Compound No. | Development of Virus Antigen Activity $ED_{50}$ (μg/ml) |
| 1 | 0.1 |
| 6 | 0.007 |

TEST EXAMPLE 4

Inhibitory activity of Compound No. 3 (OXT-G Triphosphate) on HBV-intrinsic DNA polymerase Method for measurement 1. Partial purification of HBV core particles After HB611 cells were homogenized with buffer solution for extraction shown below, the centrifugal supernatant (14000 rpm, 0° C., 30 minutes) was overlaid on 30% saccharose-containing buffer solution for extraction, which was subjected to supercentrifugation (35000 rpm, 4° C., 18 hours) to give crude core particle precipitates. The crude core particles were suspended in the buffer solution for extraction and purified by cesium chloride density-gradient centrifugation method to give partially purified core particles showing a density of 1.30 to 1.35 g/ml.

Buffer solution for extraction:
containing (0.1% Triton X-100/0.1% 2-mercaptoethanol/1 mM PMSF): 10 mM Tris-hydrochloride (pH 7.4), 1 mM EDTA, 10 mM sodium chloride 2. Measurement of HBV-intrinsic polymerase activity The partially purified core particles were added to the reaction solution shown below. After incubating at 37° C. for 2 hours in the presence of Compound No. 3 in various concentrations, dCTP was added thereto in a final concentration of 1 mM. After incubation at 37° C. for an additional an hour, proteinase K, SDS, EDTA and tRNA were added thereto in final concentrations of 0.5 mg/ml, 1%, 10 mM and 200 μg/ml, respectively, followed by incubation at 45° C. for 2 hours. Thereafter HBV-DNA was purified by phenolchloroform extraction and ethanol precipitation and then subjected to electrophoresis with 1.5% agarose. Radioactive uptake in HBV-DNA was determined by autoradiography. The autoradiogram was scanned by a densitometer to calculate the inhibitory activity of Compound No. 3 against HBV-DNA polymerase.

Reaction solution: containing 50 mM Tris-hydrochloride
(pH 7.4), 30 mM magnesium chloride, 0.1 M ammonium chloride, 0.2% 2-mercaptoethanol, 0.5% Triton X-100 and 370 KBq α-$^{32}$P-dCTP and, 200 μM each of dATP, dGTP and dTTP 3. Results

TABLE 5

| Compound No. 3 (μM) | Inhibition Rate (%) |
|---|---|
| 0 | 0.0 |
| 100 | 50.7 |
| 200 | 88.8 |
| 400 | 96.8 |

As is clear from the foregoing results, the compounds of this invention exert an excellent antiviral activity. In particular, Compound Nos. 1 and 6 have excellent anti-HIV activity and Compound No. 5 exhibits excellent antiviral activity against DNA virus such as cytomegalovirus, hepatitis B virus, herpes virus, etc.

The triphosphoric acid esters of the compounds of this invention exhibit enzyme inhibitory action in growth of virus. For example, Compound No. 2 shows reverse transcriptase inhibitory action of HIV and Compound No. 3 inhibits DNA polymerase of the aforesaid DNA virus.

What is claimed is:

1. A phosphoric acid ester of oxetanocins represented by formula (I):

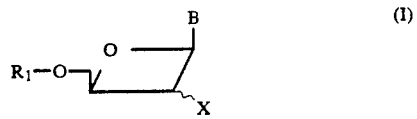

wherein R$_1$ represents

X represents hydrogen, hydroxy or hydroxymethyl, and B represents an adenine moiety, and pharmacologically acceptable salts thereof.

2. A phosphoric acid ester of oxetanocin A and 2'-dehydroxymethyloxetanocin A represented by the following formula:

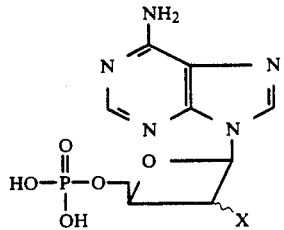

wherein X represents hydrogen or hydroxymethyl group, and pharmacologically acceptable salts thereof.

3. An antiviral composition comprising as an effective component a phosphoric acid ester of oxetanocins represented by formula (I):

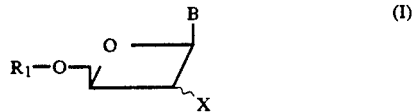

wherein R$_1$ represents

X represents hydrogen or hydroxymethyl, and B represents an adenine moiety, and pharmacologically acceptable salts thereof.

4. An anti-human immunodeficiency viral composition comprising as an effective component a phosphoric acid ester of oxetanocin according to claim 1, wherein X is hydrogen or hydroxymethyl.

* * * * *